United States Patent [19]

Phillips

[11] Patent Number: 5,744,119
[45] Date of Patent: Apr. 28, 1998

[54] PREPARATION OF A RADIOCONJUGATE FORMULATION

[75] Inventor: Christopher Phillips, Brandamore, Pa.

[73] Assignee: Sterling Winthrop, New York, N.Y.

[21] Appl. No.: 345,467

[22] Filed: Nov. 21, 1994

Related U.S. Application Data

[63] Continuation of Ser. No. 60,349, May 11, 1993, abandoned.
[51] Int. Cl.$^6$ .............................. A61K 51/08; A61K 51/10
[52] U.S. Cl. ...................... 424/1.49; 424/1.53; 424/1.69
[58] Field of Search .............................. 424/1.49, 1.53, 424/1.69

[56] References Cited

U.S. PATENT DOCUMENTS

| | | | |
|---|---|---|---|
| H819 | 9/1990 | Srivastava et al. | 530/389 |
| 4,500,508 | 2/1985 | Srivastava et al. | 424/1.1 |
| 4,741,900 | 5/1988 | Alvarez et al. | 424/85 |
| 4,831,122 | 5/1989 | Buchsbaum et al. | 530/389 |
| 4,885,363 | 12/1989 | Tweedle et al. | 540/465 |
| 5,128,119 | 7/1992 | Griffiths | 424/1.1 |
| 5,328,679 | 7/1994 | Hansen et al. | 424/1.49 |
| 5,549,882 | 8/1996 | Subramanian | 424/1.11 |

FOREIGN PATENT DOCUMENTS 9208494  5/1992  WIPO.

OTHER PUBLICATIONS

Medline #91338631, Robinson et al.
Medline #90352555, Frank et al.

*Primary Examiner*—John Kight
*Assistant Examiner*—Lara C. Kelley
*Attorney, Agent, or Firm*—Fish & Richardson P.C.

[57] ABSTRACT

The present invention is directed to a method of labeling a protein conjugate with a radionuclide to form a radioconjugate comprising reacting:

(a) the radionuclide; and (b) the protein conjugate in an acetate buffer for a time period and under conditions sufficient to form said radioconjugate.

Preferably, the protein conjugate is comprised of a complexing agent moiety and a free epsilon amino group-containing protein moiety. The completing agent moiety is preferably a terpyridine analog. The terpyridine analog is preferably TMT.

Preferably, the free epsilon amino group-containing protein moiety is an immunoreactive protein. The immunoreactive protein is preferably the monoclonal antibody ING-1.

In a preferred embodiment, the protein conjugate is TMT-ING-1, and the radionuclide is $^{90}Y$.

In a further preferred embodiment, the radioconjugate is chelated to greater than 98 percent of the radionuclide.

Preferably, the acetate buffer in which the protein conjugate is present comprises at least about 50 mM sodium acetate.

14 Claims, No Drawings

PREPARATION OF A RADIOCONJUGATE FORMULATION

This application is a continuation of U.S. application Ser. No. 08/060,349, filed May 11, 1993, now abandoned.

DESCRIPTION

1. Field of the Invention

The present invention relates to a method of preparing a radioconjugate, and more specifically to a one-step method for labeling a protein conjugate with a radionuclide to form a radioconjugate.

2. Background of the Invention

Surgical removal of cancerous tissue is not always possible and other approaches are needed to eradicate solid tumors and metastasized cells. One such approach is radioimmunotherapy. Radioimmunotherapy involves the use of targeted drug delivery using antibodies such as monoclonal antibodies (MAb's) that recognize specific cell surface receptors or antigens on tumor cells. This type of therapeutic treatment has been termed a "magic bullet" approach, as it can deliver more drug to tumor cells when conjugated to the MAb than possible by free diffusion and the site specificity allows the radionuclides to locate at very high tumor to non-tumor ratios (Wilbur et al., U.S. Pat. No. 5,057,301).

Using chelation chemistry, radioactive substances can be covalently attached to these MAb's forming a radioimmunoconjugate (RIC) molecule. These cell-targeting moieties can then be preferentially bound to the cancerous cells to cause selective cell death. The high specificity of the conjugated MAb for the target tissue minimizes the total radiation dose.

The main goal is to achieve a significant clinical response and at the same time reduce the exposure of the entire body to these toxic substances.

In the RIC molecule, a bi-functional complexing agent is covalently bonded to a MAb using isothiocyanate (NCS) chemistry. This complexing agent also chelates the radioisotope. Direct radioactive labeling of the MAb results in the radioisotope attaching at or near the antigen binding site and inactivating the NAb. Using a bifunctional chelator or complexing agent alleviates this problem.

One complexing agent useful in a RIC formulation is 4,-(3-amino-4-methoxyphenyl)-6,6"-bis[N,N-di(carboxymethyl)aminomethyl]-2,2':6',2"-terpyridine, tetrasodium salt (TMT). TMT is prepared with an isothiocyanate (NCS) group which is reactive towards an epsilon amino group on the lysine amino acid residues of the target protein. TMT overcomes the additional insufficiencies of the previously used complexing groups such as ethylene diaminetetraacetic acid (EDTA) and diethylenetriaminepentaacetic acid (DTPA).

The MAb ING-1 is a chimeric antibody consisting of a murine variable region and a human immunoglobulin constant region. ING-1 recognizes cell surface antigens expressed on colorectal cancel cells and therefore is very useful as a carrier molecule directing the destination of the RIC complex. The human immunoglobulin portion allows this antibody to more compatible to the human body than previous murine MAb's.

B72.3 is another MAb that recognizes colorectal tumor associated-antigens and has been used to form RIC molecules.

The radioisotope yttrium-90 ($^{90}Y$) is pure beta emitter which is very energetic and has the potential for treating inoperable colorectal cancer. TMT has a high specificity for this radionuclide which helps prevent the premature release of the radioisotope. This assures an adequate dose of radiation at the target tissue for radioimmunotherapy and a reduction of background noise in radioimmunodiagnostics.

In order to the $^{90}Y$ to be delivered to the target site the isotope must be bound to the RIC molecule at a level of at least 98 percent at specific activities ranging from 1 to 5 mCi/mg. Significant toxic side effects arise if $^{90}Y$ circulates in the bloodstream in an unbound form. Potentially toxic radiation can be delivered to the bone marrow, causing myelosuppression. In addition, the release of $^{90}Y$ in the bloodstream results in less radioactive treatment being delivered to the target tissue. This problem arises when the typical buffers used for forming RIC complexes are used to chelate $^{90}Y$ to TMT.

The two most commonly used buffers for forming a radioactive RIC complex are (1) a sodium phosphate buffer, and (2) a neutral or alkaline pH. These buffering systems are inappropriate for the chelation of $^{90}Y$ to TMT. When the yttrium-90 in the form of $^{90}YCl_3$ (in a dilute hydrochloric acid of 0.01–0.04N) comes into contact with a phosphate buffer it will form both a phosphate salt ($^{90}Y(PO_4)_3$) and a colloid precipitate ($^{90}Y(OH)_3$), regardless of pH. The neutral or alkaline pH does not work because above pH6, $^{90}Y$ forms the colloid $^{90}Y(OH)_3$. In the form of $^{90}Y(PO_4)_3$ or $^{90}Y(OH)_3$, $^{90}Y$ is unavailable for chelation to TNT and represents free $^{90}Y$.

In order to avoid the formation of free $^{90}Y$, the present strategy is to neutralize the $^{90}Y$ in a 0.5M acetate buffer, pH6, and then deliver the $^{90}Y$ in acetate to the phosphate buffer containing the MAB-TMT complex. While this buffering system does provide adequate labeling, the use of a multistep procedure has inherent problems.

The use of a separate buffering system adds to the risk of radioactive exposure to the radiopharmacist during both the formulation process and the disposal of additional radioactive materials. The removal of a step reduces the opportunities for error, loss of isotope or drug and introduction of contaminates. A second buffering vial does not have to be manufactured and therefore the testing and generation of specifications are avoided.

SUMMARY OF THE INVENTION

The present invention is directed to a method of labeling a protein conjugate with a radionuclide to form a radioconjugate comprising reacting:

(a) the radionuclide; and (b) the protein conjugate in an acetate buffer for a time period and under conditions sufficient to form said radioconjugate.

Preferably, the protein conjugate is comprised of a completing agent moiety and a free epsilon amino group-containing protein moiety. The completing agent moiety is preferably a terpyridine analog. The terpyridine analog is preferably TMT.

Preferably, the free epsilon amino group-containing protein moiety is an immunoreactive protein. The immunoreactive protein is preferably the monoclonal antibody ING-1.

In a preferred embodiment, the protein conjugate is TMT-ING-1, and the radionuclide is $^{90}Y$.

In a further preferred embodiment, the radioconjugate is chelated to greater than 98 percent of the radionuclide.

Preferably, the acetate buffer in which the protein conjugate is present comprises at least about 50 mM sodium acetate.

DETAILED DESCRIPTION OF THE INVENTION

The present invention is directed to a method of labeling a protein conjugate with a radionuclide to form a radioconjugate comprising reacting:

(a) the radionuclide; and (b) the protein conjugate in an acetate buffer for a time period and under conditions sufficient to form said radioconjugate.

A protein conjugate comprises a two-part protein molecule, each part covalently attached to the other one part of the protein conjugate comprises a targeting moiety that allows for the non-covalent three dimensional binding between complementary portions of two molecules.

Examples of a targeting moiety include a polynucleotide sequence, such as DNA or RNA, an antibody molecule or its fragments, a lectin, a hormone, a receptor molecule, an enzyme, or a binding ligand system such as biotin/avidin.

Targeting moieties useful in the present invention must have an available, or free, epsilon amino acid group, such as on the amino acid lysine, in order to covalently attach to the second part of the protein conjugate, the complexing agent moiety.

A complexing agent functions to bind the targeting moiety of the protein conjugate to the radionuclide portion of the radioconjugate. A complexing agent is a compound containing donor atoms that can combine by coordinate bonding with a metal atom to form a cyclic structure called a chelation complex or a chelate. See Kirk-Othmer Encyclopedia of Chemical Technology, vol. 5, 339–368.

The complexing agent moiety is preferably a terpyridine analog, as disclosed in WO 92/08494 (PCT/US91/08253). Non-limiting examples of terpyridine analog complexing agents include:

4'-(3-amino-4-methoxyphenyl)-6,6"-bis(N,N-di-(carboxymethyl) aminomethyl)-2,2':6'2"-terpyridine;

4'-(4-methoxyphenyl)-6,6"-bis[N,N-di-(carboxymethyl) aminomethyl]-2,2':6'2"-terpyridine;

4'-(4-amino-3-methoxyphenyl)-6,6"-bis[N,N-di-(carboxymethyl) aminomethyl]-2,2':6'2"-terpyridine;

4'-(3-methoxyphenyl)-6,6"-bis[N,N-di(carboxymethyl)-aminomethyl]-2,2':6'2"-terpyridine;

4'-(3,4-dimethoxyphenyl)-6,6"-bis(N,N-di-(carboxymethyl) aminomethyl)-2,2':6'2"-terpyridine;

4'-(3,4-methylenedioxyphenyl)-6,6"-bis(N,N-di-(carboxymethyl) aminomethyl)-2,2':6'2"-terpyridine;

4'-(4-methoxyphenyl)-6-aminomethyl-6"-carboxymethylaminomethyl-2,2':6'2"-terpyridine;

4'-(4-methoxyphenyl)-6,6"-bis (carboxymethylaminomethyl)-2,2':6'2"-terpyridine;

4'-(4-methoxyphenyl)-6-aminomethyl-6"-[N,N-di-(carboxymethyl)aminomethyl]-2,2':6'2"-terpyridine; and 4'-(4-methoxyphenyl)-6-carboxymethylaminomethyl-6"-[N,N-di-(carboxymethyl) aminomethyl] -2,2':6'2"-terpyridine.

The terpyridine analog is preferably 4'-(3-amino-4-methoxyphenyl)-6,6"-bis[N,N-di-(carboxymethyl) aminomethyl]-2,2':6'2"-terpyridine (TMT).

A radioconjugate is comprised of a protein conjugate labeled with a radionuclide, i.e. one in which the complexing agent moiety of the protein conjugate has formed a complex with a radionuclide.

A radionuclide is preferably a radioactive metal ion isotope which can be an isotope useful in therapy or in diagnostic imaging. The radioactive metal isotope can be an ion of an isotope of a metal selected, for example, from Sc, Fe, Pb, Ga, Y, Bi, Mn, Cu, Cr, Zn, Ge, Mo, Tc, Ru, In, Sn, Re, Sr, Sm, Lu, Du, Sb, W, Re, Po, Ta and Ti ions. Preferred isotopes of radioactive metal ions include $^{44}$Sc, $^{64,67}$Cu, $^{111}$In, $^{212}$Pb, $^{68}$Ga, $^{90}$Y, $^{153}$Sm, $^{212}$Bi, $^{99m}$Tc and $^{138}$Re. Especially preferred is $^{90}$Y.

Preferably, the protein conjugate is comprised derivatives of a complexing agent moiety and a free epsilon amino group-containing protein moiety. Thus, the complexing agent moiety is covalently attached to the protein moiety via the free epsilon amino group.

An acetate buffer can be formed by placing into an aqueous solution an acetate-containing compound, for example, sodium acetate, potassium acetate, or magnesium acetate. Preferably, sodium acetate is used.

Preferably, the free epsilon amino group-containing protein moiety is an immunoreactive protein. An immunoreactive protein, as is well known in the art, comprises an antibody or its fragments, all of which contain an antibody combining site. An immunoreactive protein also comprises an antigen capable of binding to an antibody combining site.

The antibody may be polyclonal or monoclonal, but is preferably monoclonal. Preferred antibodies include antibodies to tumor-associated antigens. Specific non-limiting examples include B72.3 and related antibodies (described in U.S. Pat. Nos. 4,522,918 and 4,612,282), which recognize colorectal tumors; 9.2.27 and related anti-melanoma antibodies; D612 and related antibodies which recognize small cell lung carcinomas; NRLU-10 and related antibodies which recognize small cell lung carcinomas and colorectal tumors (pancarcinoma); 7E11C5 and related antibodies which recognize prostate tumors; CC49 and related antibodies which recognize colorectal tumors; TNT and related antibodies which recognize necrotic tissue; PR1A3 and related antibodies which recognize colon carcinoma; ING-1 and related antibodies, which recognize colorectal tumors (described in WO-A-90/02569); B174 and related antibodies which recognize squamous cell carcinomas; B43 and related antibodies, which are reactive with certain lymphomas and leukemias; and anti-HLB and related monoclonal antibodies.

The immunoreactive protein is preferably the monoclonal antibody ING-1.

In a preferred embodiment, the protein conjugate is TMT-ING-1, and the radionuclide is $^{90}$Y. The resulting radioconjugate comprises TMT and ING-1, covalently linked, and $^{90}$Y chelated to the protein conjugate via TMT. In this embodiment, the radioconjugate can also be referred to as a radioimmunoconjugate.

In a further preferred embodiment, the radioconjugate is chelated to greater than 98 percent of the radionuclide. Thus, the amount of free radionuclide is less than 2 percent of the starting amount.

Preferably, the acetate buffer in which the protein conjugate is present comprises at least about 50 mM sodium acetate. The molarity of the acetate buffer depends upon the other components of the buffering system, including the amount of protein conjugate, the amount of radionuclide, and the amount of any other buffering agents.

The molarity of the acetate buffer can range from about 10 mM to about 150 mM, and more preferably from about 50 mM to about 100 mM, and most preferably, is about 50 mM.

The pH value of the buffered solution is dependent, inter alia, on such factors as the pKa of the underlying buffer, the presence of other components, and the adjustments made by the addition of acid and/or base. The pH value of the acetate buffer may range from about 4 to about 10, and more preferably from about 5 to about 9, and is preferably about 5.6.

The invention described herein is a one-step method for the formulation of a radioconjugate which avoids the formation of unacceptable levels of unbound radionuclide. With the reduction of free radionuclide, potentially toxic effects derived from unbound radionuclide are avoided and more of the therapeutic agent is available at the treatment site.

Instead of the protein conjugate being in a phosphate buffer and requiring an acetate buffer to neutralize it, it is placed in a vial containing the acetate buffer from the start. By using this buffering system, the radionuclide can be directly added to the vial containing the protein conjugate without pretreatment of the isotope solution, regardless of the antibody or other protein used in the protein conjugate. The only requirement for the protein in this direct addition formulation is that there is an available an attachment group such as an epsilon amino group on, for example, a lysine amino acid for the covalent attachment to the complexing agent and that the conjugate is introduced into the specified buffer. Given this, any protein should provide a similar result: a radioconjugate molecule labeled with a radionuclide at a level of at least 98 percent.

The use of a one-step process to prepare the formulation eliminates unnecessary exposure to harmful radiation on the part of the radiopharmacist, reduces opportunities for error and loss of isotope or drug and removes additional sources of contamination. In addition to being used as a therapeutic treatment, this radioconjugate formulation has the potential to be used in the field of diagnostic imaging.

The following examples further illustrate the invention and are not to be construed as limiting of the specification and claims in any way.

Example 1: Direct vs. Indirect Addition of $^{90}Y$

A sterile aqueous solution containing the B72.3-TMT protein conjugate complex consists of: B72.3 at a concentration of 5 mg/ml with TMT present on the MAb in a molar ratio of 1:8, the surfactant Pluronic F-68 at 0.02 percent w/v and 150 mM NaCl. The conjugate is introduced into the formulation either by desalting through a G-25 Sephadex column that has been equilibrated with the buffer or by dialfiltration using a tangential flow apparatus with 30,000 Molecular Weight Cutoff membranes.

The essential difference between the direct and indirect addition formulations is the buffering system. The percentage of $^{90}Y$ that is bound to the RIC complex is measured on a Bioscan using Instant Thin Layer Chromatography (ITLC) or via Size Exclusion High Performance Liquid Chromatograph with UV radiation detectors.

A. Direct Addition Formulation:

The buffer system for the RIC complex is sodium acetate in a concentration of either 50 mM, 75 mM or 100 mM. The radionuclide $^{90}Y$ is directly added to the vial containing the RIC complex and the solution is titrated to pH 5.6 with glacial acetic acid.

B. Indirect Addition Formulation:

The radionuclide $^{90}Y$ (50 mCi/ml) is neutralized with 0.04N HCl. One part of this solution is then added to two parts of 0.5M sodium acetate, pH 6. The resulting solution contains 0.33M sodium acetate and $^{90}Y$ at 33 mCi/ml. This is then added to the B72.3-TMT solution containing 10 mM phosphate, pH 7 and 150 mM NaCl.

TABLE 1

| Acetate Buffer | Direct Addition* | Indirect Addition* |
|---|---|---|
| 50 mM | 99.5 | 96.6 |
| 75 mM | 99.3 | 99.0 |
| 100 mM | 99.2 | 99.1 |

*Percentage of $^{90}Y$ bound.

Table 1 show that the direct addition formulation gives comparable results to the indirect addition formulation. In both cases, adequate labeling of the RIC molecule is achieved. At the same time, the number of steps used to obtain an acceptable level of bound $^{90}Y$ is reduced with the direct formulation Example 2: Stability of $^{90}Y$ Bound to ING-1-TMT The ING-1-TMT RIC molecules were manufactured over a period of time and then tested on the same date. These lots were labeled with $^{90}Y$ from MediPhysics at 1 mCi/mg via the direct labeling method. The percent $^{90}Y$ bound was measured using ITLC at 1-, 2-, 3- and 4-hour intervals.

The composition of the formulation used for the ING-1-TMT is: 100 mM acetate buffer, 150 mM NaCl, 0.02 percent Pluronic F-68, titrated to pH 5.6 with glacial acetic acid. The conjugate is introduced into the formulation either by desalting through a G-25 Sephadex column that has been equilibrated with the buffer or by dialfiltration using a tangential flow apparatus with 30,000 Molecular Weight Cutoff membranes. At this point the $^{90}Y$ can be added.

TABLE 2

| Sample No.[1] | Weeks Held | 1 Hr.[2] | 2 Hr.[2] | 3 Hr.[2] | 4 Hr.[2] |
|---|---|---|---|---|---|
| 1 $^{90}Y$ Stock |  | 0.2 | 0.3 | 0.2 | ND[3] |
| 2 PHP-2505-086 | 27 | 85 | 83 | 96 | 97[4] |
| 3 PHP-2505-164C | 21.5 | 97 | 97 | 98 | 98 |
| 4 PHP-2505-181A | 19 | 98 | 99 | 99 | 99 |
| 5 POR-2522-036C | 15.5 | 93 | 92 | 97 | 98 |
| 6 POR-2552-136A | 6.5 | 96 | 99 | 98 | 98 |
| 7 BNA-2525-033A | 6 | 97 | 98 | 96 | 98 |
| 8 BNA-2525-033C | 6 | 98 | 98 | 98 | 99 |
| 9 POR-2522-142 | 5.5 | 97 | 99 | 98 | 98 |
| 10 POR-2537-019 | 1 | 99 | 99 | 99 | 99 |
| 11 POR-2537-025 | 0.5 | 99 | 97 | 100 | 99 |

[1]The sample name is derived from the letters of the experiments name (e.g., PHP), the actual number of the notebook (e.g., 2505), the page number (e.g., 164) and a specific reference on the page if needed (e.g., C).
[2]Percentage $^{90}Y$ bound.
[3]ND: Not Done.
[4]The lower values in this sample may have arisen from the adulteration of the sample with metal, problems with the ITLC strip or the application method of analysis.

The data in Table 2 show that the ING-1-TMT complex is stable for at least 21.5 weeks. The percent $^{90}Y$ bound remains at the acceptable level of 98 percent or better, thereby avoiding the possible toxic effects from circulating free $^{90}Y$.

The foregoing specification, including the specific embodiments and examples is intended to be illustrative of the present invention and is not to be taken as limiting. Numerous other variations and modifications can be effected without departing from the true spirit and scope of the present invention.

I claim:

1. A method of labeling a protein conjugate comprising a targeting moiety covalently bonded to a terpyridine complexant moiety, with a metal radionuclide to form a radioconjugate comprising:

(a) providing the protein conjugate in an acetate buffer and (b) adding a metal radionuclide to the protein conjugate so as to react the metal radionuclide; and the protein conjugate.

2. The method of claim 1 wherein said targeting moiety is a free epsilon amino group-containing protein moiety.

3. The method of claim 1 wherein said terpyridine complexant moiety is TMT.

4. The method of claim 2 wherein said free epsilon amino group-containing protein moiety is an immunoreactive protein.

5. The method of claim 4 wherein said immunoreactive protein is ING-1.

6. The method of claim 2 wherein said protein conjugate is TMT-ING-1.

7. The method of claim 1 wherein said metal radionuclide is $^{90}Y$.

8. The method of claim 1 wherein said radioconjugate is chelated to greater than 98 percent of said metal radionuclide.

9. The method of claim 1 wherein said acetate buffer comprises at least about 50 mM sodium acetate.

10. The method according to claim 1 wherein, prior to (b), the metal radionuclide is present in a solution which does not contain a buffer.

11. The method according to claim 1 wherein the metal radionuclide is present in a solution which is not pretreated prior to being introduced into the protein conjugate.

12. In a method of labeling a protein conjugate comprising a targeting moiety covalently bonded to a terpyridine complexant moiety, with a metal radionuclide to form a radioconjugate, the improvement comprising adding the metal radionuclide to the protein conjugate which is in an acetate buffer.

13. The method according to claim 12 wherein the metal radionuclide is present in a solution which does not contain a buffer.

14. The method according to claim 12 wherein the metal radionuclide is present in a solution which is not pretreated prior to being introduced into the protein conjugate.

* * * * *